United States Patent
Goh et al.

(10) Patent No.: US 7,782,193 B2
(45) Date of Patent: Aug. 24, 2010

(54) SYSTEM FOR MEASURING AND TRACKING AT LEAST ONE PHYSIOLOGICAL PARAMETER AND A MEASURING DEVICE FOR DOING THE SAME

(75) Inventors: Zenton Goh, Singapore (SG); Sian Sheng Neo, Singapore (SG); Hon Cheong Ng, Singapore (SG); Soh Min Lim, Singapore (SG)

(73) Assignee: Cadi Scientific Pte Ltd., Singapore (SG)

( * ) Notice: Subject to any disclaimer, the term of this patent is extended or adjusted under 35 U.S.C. 154(b) by 292 days.

(21) Appl. No.: 11/997,685

(22) PCT Filed: Oct. 25, 2005

(86) PCT No.: PCT/SG2005/000367

§ 371 (c)(1),
(2), (4) Date: Feb. 1, 2008

(87) PCT Pub. No.: WO2007/050037

PCT Pub. Date: May 3, 2007

(65) Prior Publication Data

US 2008/0194926 A1 Aug. 14, 2008

(51) Int. Cl.
*G08B 1/08* (2006.01)
(52) U.S. Cl. .............. 340/539.12; 340/539.11; 340/573.1
(58) Field of Classification Search .......... 340/539.12, 340/539.11, 539.1, 573.5, 573.7
See application file for complete search history.

(56) References Cited

U.S. PATENT DOCUMENTS

| 5,348,008 | A | 9/1994 | Bornn et al. |
| 5,997,476 | A | 12/1999 | Brown |
| 6,084,522 | A * | 7/2000 | Addy ................. 340/630 |
| 6,544,174 | B2 | 4/2003 | West et al. |
| 6,589,170 | B1 | 7/2003 | Flach et al. |
| 6,606,993 | B1 * | 8/2003 | Wiesmann et al. ..... 128/204.23 |
| 6,629,776 | B2 | 10/2003 | Bell et al. |
| 6,731,962 | B1 | 5/2004 | Katarow et al. |
| 2002/0008625 | A1 * | 1/2002 | Adams et al. ............ 340/573.1 |
| 2004/0215098 | A1 | 10/2004 | Barton et al. |
| 2009/0076341 | A1 * | 3/2009 | James et al. ................. 600/301 |

FOREIGN PATENT DOCUMENTS

| EP | 0 025 653 A1 | 3/1981 |
| WO | 0145014 A1 | 6/2001 |
| WO | 2005006970 A1 | 1/2005 |

* cited by examiner

*Primary Examiner*—Toan N Pham
*Assistant Examiner*—Travis R Hunnings
(74) *Attorney, Agent, or Firm*—Steven J. Hultquist; Intellectual Property/Technology Law

(57) ABSTRACT

A measurement device (26, 28, 800, 900) for measuring at least one physiological parameter comprising an integrated switching device being operable by a non-radio frequency switching activation signal generated by an external switching activation device (1000, 1100), a measurement unit for measuring at least one physiological parameter and a radio frequency signal transmitting device for transmitting a measured value of the at least one physiological parameter wherein the measurement unit and/or radio frequency signal transmitting device are/is activated if the integrated switching device is in a first switching status and deactivated if the integrated switching device is in a second switching status.

39 Claims, 11 Drawing Sheets

FIG. 11
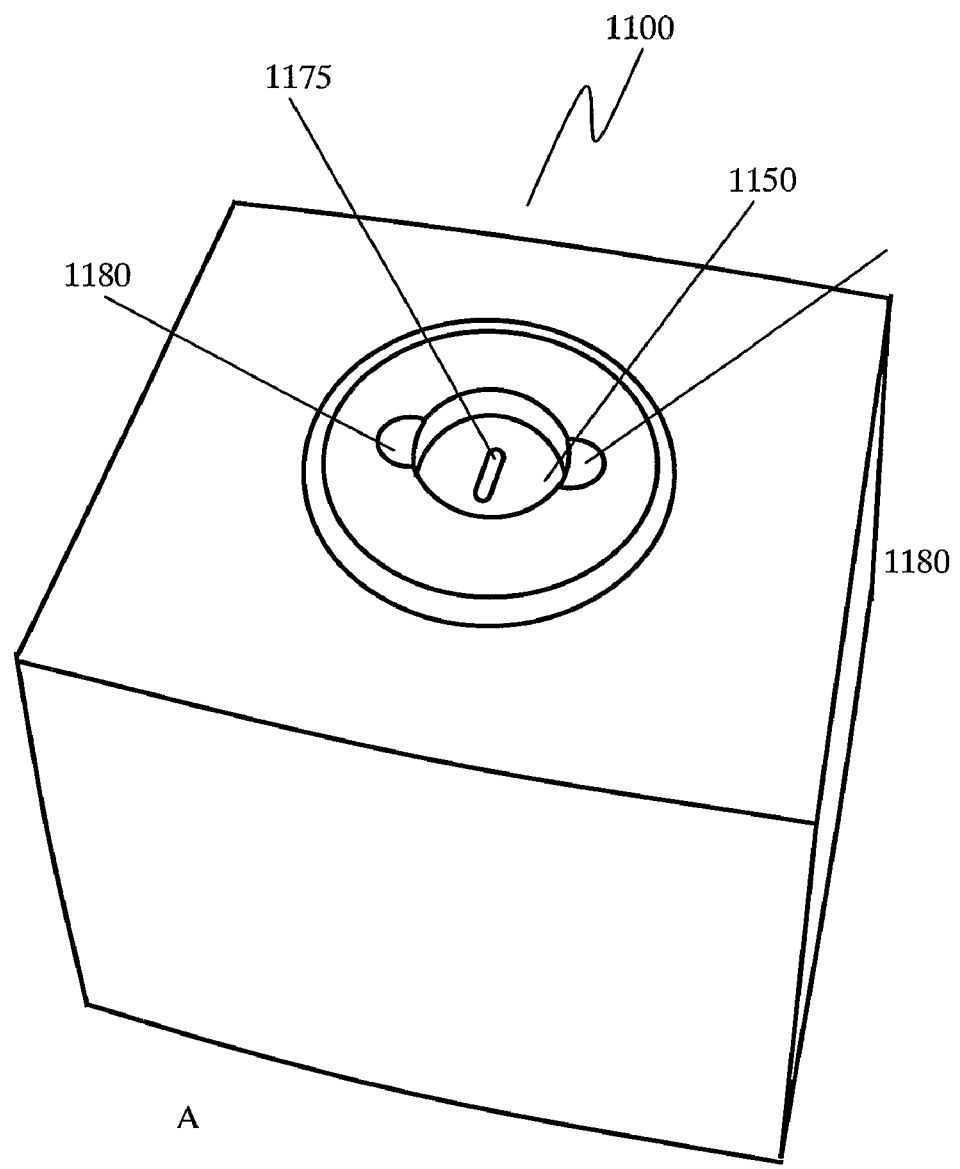
A
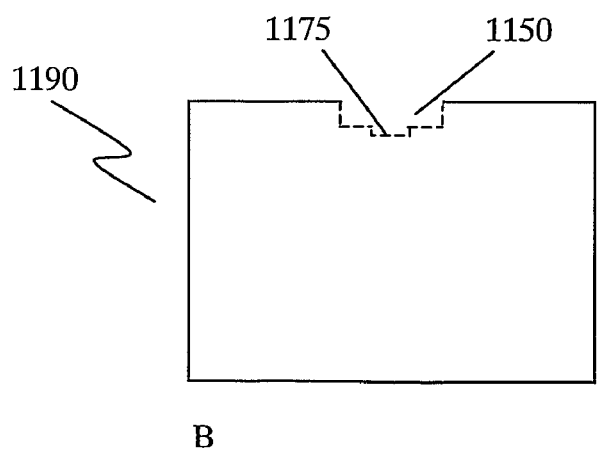
B

SYSTEM FOR MEASURING AND TRACKING AT LEAST ONE PHYSIOLOGICAL PARAMETER AND A MEASURING DEVICE FOR DOING THE SAME

CROSS-REFERENCE TO RELATED APPLICATION

This application is filed under the provisions of 35 USC §371 as a U.S. national phase application of International Application No. PCT/SG05/00367 filed Oct. 25, 2005. The disclosure of such international application is hereby incorporated herein by reference in its entirety, for all purposes.

The present invention relates to a measuring device used for the measurement of at least one physiological parameter of a person. More specifically, the present invention relates to a temperature measuring device and a system for remotely monitoring the temperature measurements as obtained from the device.

Medical personnel are required to take readings of various physiological parameters from each patient at various time-points throughout the course of the day. The medical personnel may be required to measure the temperature, blood pressure, respiratory status and pulse rate of a patient as various time intervals, for example. However, when a medical facility lacks sufficient medical staff for measuring and recording the physiological data of patients on a regular basis, a systematic measurement and recordation of the physiological data of patients may not be possible. This may lead to a deterioration of patient care standards within a medical facility as it would prevent medical staff from preempting the onset of various complications, said complications being detectable through the deterioration (or irregularity) of the basic physiological parameters such as the blood pressure, heart rate, temperature and respiratory functions from the optimal levels.

The average hospitalized population in the United States according to the National Center for Health Statistics (NCHS), for example, is approximately 33 million patients annually, i.e. approximately 11 percent of the population of the United States. With such a high proportion of the population being hospitalized annually, it is often found that the resources of a hospital are stretched to capacity in order to cope with the large numbers of patients that require care.

The situation, as described above, is constantly faced by many hospitals in both the developed and developing countries. Presently, much of the time of medical staff is occupied not only with dealing with emergencies but also with the routine measurement of blood glucose levels, blood oxygen and carbon dioxide levels, blood pressure, pulse rate, temperature and respiration rates of patients apart from existing duties such as aiding in the cleanliness and medication of the patients concerned.

Attempts to automate the routine portions of the job of a medical caregiver include providing an automated measurement system of physiological parameters such as blood pressure, respiration rate and temperature by transceiver devices. Such systems are disclosed in U.S. Pat. Nos. 6,589,170, 6,544,174, 5,997,476, PCT application WO 01/45014 A1, and US Patent application US 2004/0215098 A1.

U.S. Pat. No. 6,589,170 discloses a patient monitoring system that comprises a controller, a receiving station and a transceiver sensor located within a local area network (LAN) that can monitor a physiological parameter of a patient. The transceiver is attached to the patient and the document further discloses that the transceiver, which maintains multiple links to various receiving stations, utilizes the time division multiple access (TDMA) protocol in order to transmit and receive data from the LAN to which it is linked FIG. 2 of the US patent shows the attachment of one such transceiver. Based on the design of the transceiver, regardless of where it is placed, be it on the front or rear of the torso, it hinders the mobility and comfort of a patient.

U.S. Pat. No. 6,544,174 discloses a patient monitoring system that comprises a local area network (LAN), a wireless transceiver sensor and control devices to receive and monitor the physiological parameters that are measured by the sensor. The transceiver utilizes the TCP/IP and UDP protocols to transmit and receive data from the control devices via the LAN. The control device is configured to monitor the physiological parameters received from the transceiver against predetermined threshold values, the frequency of the transmissions and the location of the transmissions, which correlates to the location of the patients as well.

U.S. Pat. No. 5,997,476 discloses a networked system for the interactive communication and remote monitoring of individuals. In this system, the patient is required to provide an input to the remote interface. The remote interface transmits the input of the patient to a server where the responses are analyzed by a script program. The server responds by transmitting messages back to the patient in order to obtain more data or to advise a patient accordingly. The frequent transmissions and "listening" of the receiver of such a device within said system leads to a consumption of a substantial amount of battery power. In order for the system to function effectively, the remote device contained therein usually requires a large power source or require frequent maintenance in order to function for the period required.

Similarly, the apparatus and system disclosed in PCT application WO 01/45014 A1 also requires the patient to interact with the remote monitoring device. This happens as the patient provides responses to queries that are directed to him by the server. The server runs an algorithm that queries the patient, collects and analyzes the responses of a patient and forwards the status of the patient to a health specialist.

US Patent application 2004/0215098 A1 discloses a unidirectional telesensor sandwiched between a first and second layers of a skin-compatible adhesive material. The telesensor, which may be a temperature sensor, periodically measures the temperature of the body and transmits the measurement information via a radio frequency (RF) link A receiving unit receives the transmission and derives the temperature. The device disclosed herein may be activated by either by optical or RF means.

In the implementation of such systems as mentioned above, systemic problems faced include collisions of data packets due to simultaneous transmissions from at least two different transceivers, a lack of sufficient wireless network coverage, and bulky transceivers that hinder the mobility of the patient and therefore, are not user-friendly. Other possible shortcomings may be sensor devices prone to tampering such as premature or unauthorized activation/deactivation of sensor devices and a limitation to the number of patients that can be effectively monitored at any one time.

However, there is still a need to provide a cost effective and reliable system capable of measuring, receiving, recording and processing at least one physiological parameter of at least one person remotely or otherwise. There is also a further need to provide a system, wherein said system provides for a physiological parameter-measuring device that is user-friendly, cost effective and has the capability to remotely measure physiological parameters. In addition, the measuring device should also be functionally efficient to prevent the loss of data during transmission while also capable of tracking the location of said patients within a given area.

The system, devices and method having the features of the respective independent claims solve the above-mentioned problems.

Such a system for measuring at least one physiological parameter of at least one person includes a switching activation device and at least one measuring device. The switching activation device is designed such that when brought into contact with the at least one measuring device, the at least one measuring device undergoes a switching. In this respect, it should be noted that the switching activation device determines/controls the switching status of the measuring device. Furthermore, in this context, contact may refer to either direct physical contact or contact established by magnetic and electromagnetic radiation, for example. Accordingly, the measuring device may switch between a first switching status and a second switching status or vice versa.

In one example, the first switching status may have the following two sub-statuses:
 (a) An initialization sub-status, and
 (b) An "ON" sub-status, which the measuring device enters upon completion of initialization.

In another example, the second switching status may also have the following two sub-statuses:
 (a) A de-initialization sub-status, and
 (b) AQ "OFF" sub-status.

The measuring device used in the system of the invention includes an integrated switching mechanism and a radio frequency signal-transmitting device. The radio frequency signal-transmitting device may be activated by the integrated switching mechanism. If the integrated switching mechanism is in the first switching status or the second switching status, the radio frequency signal-transmitting device may be activated or deactivated accordingly.

The above-mentioned integrated switching mechanism is operable by non-radio frequency activation means that may be provided by the switching activation device. The non-radio frequency activation means may be either mechanical means, magnetic means or a combination of both.

Generally, with regard to mechanical means, every mechanical activation means may be utilized. Examples of mechanical non-radio frequency activation means may be a pressure switch, a contact switch, a slider switch, a rocker switch, a push-button switch and a rotary switch.

Typically, for magnetic means, every magnetic activation means may be utilized. Examples of magnetic non-radio frequency activation means may be a magnetic relay switch, a reed switch and a momentary contact switch. In a further embodiment, the system may further include a separate registration unit that is adapted to function in unison with the switching activation device. The registration unit may be a microprocessor capable of registering (or deregistering) the measuring device when the measuring device is in either the first or second switching state respectively.

In another embodiment, the system may further comprise of at least one receiver unit. The receiver unit may be adapted to receive a data packet that is transmitted periodically by the at least one measuring device.

In a further embodiment, the system may further comprise at least one control unit. The control unit is adapted to receive data packets from the receiver unit. The control unit may also be adapted to function as a registration unit as well.

The at least one measuring device has stored therein, on a memory chip, a unique identifier. The unique identifier allows the registration unit to recognize the at least one measuring device during the registration process. Alternatively, in the embodiment wherein the control unit functions at the registration unit, the control unit may recognize the unique identifier during the registration process. The registration unit is adapted to recognize and record an association between the unique identifier of the at least one measuring device and the particulars of a person.

Typically, components of the system such as the measuring device, registration unit, receiver unit and control unit, for example, are in communication using a radio frequency (RF) wireless local area network (WLAN) that utilizes one or a multitude of protocols such as WiFi, ZigBee, Bluetooth or other proprietary protocols, for example. Alternatively, the components of the system may utilize a wired local area network (LAN) using one or a combination of protocols such as RS-232, RS-485, the Ethernet or a combination of wireless and wired local area network protocols.

Once the integrated switching mechanism of the measuring device is activated to the first switching status, the RF signal-transmitting device will transmit the unique identifier to the receiver unit. The receiver unit will then relay the unique identifier to the control unit. The control unit will in turn relay the unique identifier to the registration unit for registration into the communication network. The registration unit may then assign the identity of a patient being monitored to the newly registered unique identifier of the measuring device thereby personalizing the said measuring device.

The data packet transmitted by the measuring device to the receiver unit, or registration unit as in the case of the registration process, comprises the above-mentioned unique identifier of the at least one measuring device, a signal/data field, at least one measured physiological parameter value and optionally, the battery status of the at least one measuring device.

In one embodiment, when the measuring device is first brought into contact with the switching activation device during registration, the measuring device enters the initialization status of the first switching status and transmits registration packets periodically. This is referred to as the initialization sub-status of the measuring device, as mentioned above. Each registration packet contains the signal/data field, which contains the relevant data to indicate to the control unit that registration is taking place or is initiated. The control unit in turn will create an association between the measuring device being registered and a profile/person to which said measuring device will be attached to.

Subsequently, when in this embodiment the measuring device is removed from the switching activation device, it then enters the "ON" sub-status of the first switching status and continues to transmit except that it now transmits information packets periodically to the control unit. Each information packet, as with the registration packet, still contains the signal/data field. However, the signal/data field of the information packet now only includes data specific to the information transmission mode, and not to the registration mode or de-registration mode. In other words, the information now transmitted to the control unit pertains rather to the person to which the measuring device is attached to and may only relate to only a physiological parameter such as the temperature, heart rate or pulse rate, for example.

When the measuring device in this embodiment, is in the information transmission mode (or "ON" sub-status), and is placed once again in contact with the switching activation device, it enters the de-initialization sub-status of the second switching status and begins to transmit de-registration packets periodically to the control unit. Each de-registration packet also contains the signal/data field, but in this case the field indicates the de-registration of the measuring device to the control unit. Finally, when de-registration is complete, the measuring device enters the "OFF" sub-status of the second switching status.

In an alternative embodiment, when the measuring device is first brought into contact with the switching activation device during registration, the measuring device also enters the initialization status of the first switching status. However, in instead of continuous transmission of registration packets (until the contact with the switching activation device is stopped) the measuring device transmits a predetermined number of registration packets, for example, 10, 15 or 20 registration packets. This status is referred to as the initialization sub-status of the measuring device. Each registration packet contains the signal/data field, which contains the relevant data to indicate to the control unit that registration is taking place or is initiated. Also, in this embodiment the control unit in turn will create an association between the measuring device being registered and a profile/person to which said measuring device will be attached to. As soon as the predetermined numbers of registration packets have been transmitted, the measuring device automatically enters the second sub-status of the first switching status, even if it still remains in contact with the switching activation device. In the second sub-status of the first switching status, the measuring device now transmits information packets.

In this respect, the measuring device continues to transmit said information packets periodically to the control unit. Each information packet, as with the registration packet, still contains the signal/data field. However, also in this embodiment the signal/data field of the information packet now only includes data specific to the information transmission mode, and not to the registration mode or de-registration mode. In other words, the information now transmitted to the control unit pertains rather to the person to which the measuring device is attached to and may only relate to only a physiological parameter such as the temperature, heart rate or pulse rate, for example.

When the measuring device in this embodiment is in the information transmission mode (or "ON" sub-status), and is placed once again in contact with the switching activation device, it enters the de-initialization sub-status of the second switching status and begins to transmit a predetermined number of de-registration packets (for example 10, 15 or 20 de-registration packets) periodically to the control unit. Each de-registration packet also contains the signal/data field, but in this case the field indicates the de-registration of the measuring device to the control unit. Finally, when predetermined number of de-registration packets has been transmitted, the measuring device enters the "OFF" sub-status of the second switching status.

The embodiment of the invention as described earlier requires direct user intervention for switching between the respective sub-statuses, i.e. the measuring device cannot switch between the initialization sub-status to the "ON" sub-status without being removed from the switching activation device, for example. Correspondingly, this measuring device also cannot switch from the de-registration sub-status into the "OFF" sub-status without being removed from the switching activation device after deregistration is complete. Accordingly, this embodiment advantageously allows the user to determine when the measuring device may switch between the various sub-statuses described.

In yet another embodiment, when the measuring device is in the first switching status, the data packets transmitted to the controller unit include data/signal fields. However, in this embodiment, the data/signal fields may include both registration data as well as the measured physiological data. Accordingly, the first switching status in this embodiment, unlike the first switching status of the previous embodiment, comprises a single sub-status. In the single sub-status, the measuring device, when in contact with the switching activation device, begins to transmit both registration data as well as measured physiological data as well.

It follows from above that the second switching status of the measuring device of the above embodiment also comprises of a single sub-status. When the transmitting measuring device is placed on the switching activation device, it transmits a de registration packet and subsequently, shuts off.

The measuring device may not transmit the battery status along with the various data packets that are transmitted during the respective four sub-statuses. Instead, the battery contained therein may be adapted to perform a fixed number of transmissions. Accordingly, in such an embodiment, the number of transmissions made correlates to the battery status in that said battery status may be derived from the number of transmissions made and the number of transmissions that the measuring device may still make. As an illustrative example, should a battery be adapted to perform ten transmissions and has already performed five of said ten possible transmissions, it may be concluded that the battery is at fifty percent of its original strength.

In this embodiment of monitoring the battery status, the control unit may be tasked with monitoring the number of transmissions made by each registered measuring device. In this regard, the control unit may perform a comparative operation and determine that the remaining battery power of a measuring device is low. Subsequently a warning may be issued by the system to any administrators instructing them to replace the measuring device or the battery contained therein.

In order to increase the reliability of the transmission from the at least one measuring device to the receiver unit, the measuring device may utilize an anti-collision algorithm to minimize the occurrence that two measuring devices transmit simultaneously thereby resulting in a collision of data packets at the receiver unit. Examples of the aforementioned anti-collision algorithm that may be used with the present invention are disclosed in U.S. Pat. No. 6,629,776 and U.S. Pat. No. 6,589,170 to name only a few. Apart from these known algorithms, the present invention discloses a novel anti-collision algorithm. This anti-collision algorithm utilized by the present invention, provides for each measuring device, a pseudo-randomized time-slot to periodically transmit a data packet. In one exemplary embodiment of this algorithm, the likelihood of a measuring device having a data packet collision occurring in a scenario where 20 measuring devices are within range of a receiver unit is 1.855%. The likelihood of the same measuring device having a data packet suffering a second consecutive collision decreases to 0.0344%. The anti-collision algorithm of the invention is discussed in greater detail below.

Upon receiving the data packet from the measuring device, the receiver unit appends a time and date of receipt information (henceforth known as time-code) to each data packet that it receives. In order to accomplish an accurate time coding of all data packets sent to the various receiver units, each receiver unit comprises an internal clock. The internal clocks of all the receiver units are synchronized with the internal clock of the control unit. The receiver units are programmed such that when reset, the startup sequence dictates that the reset receiver units will automatically request such synchronization from the control unit. Alternatively, the receiver units may also conduct a synchronization procedure upon receiving such instructions from the control unit. The synchronization process occurs at least every twenty-four hours or as and when deemed necessary.

In addition to each receiver unit having an internal clock, each receiver unit has stored therein its own unique identifier. When a receiver unit, in addition to the time-code, receives a data packet the receiver unit appends the unique receiver identifier to the data packet prior to forwarding the data packet to the control unit. Such repeated coding allows the control unit to record which receiver unit transmitted a particular data packet and which particular measuring device said data packet originated from. This also allows the control unit to track the position of each measuring device (as each receiver unit is located in a specific area). Should a particular data packet from a particular receiver unit indicate that a patient has a physiological anomaly, using the time-code information, all other data packets that were transmitted by that particular receiver from other measuring devices can be traced. This means that other patients who may have been in the immediate vicinity of the anomalous patient can be identified for closer observation and immediate treatment rendered, if necessary.

The receiver unit may be linked to the control unit by cables taken from the group consisting of, but not limited to, universal serial bus (USB) cables, serial and parallel port cables, IEEE 1394 Firewire cables and standard local area network cables such as Ethernet or RS-485 serial communication interface cables. Alternatively, the receiver unit may also be linked to the control unit via wireless communication means as well.

The control unit in the system may include at least one database storage unit, at least one server unit and at least one; personal computer unit. The database storage unit receives the transmitted data packets from each measuring device via the receiver unit and stores them accordingly. It also serves as an information retrieval system such that medical specialists, for analysis purposes, may retrieve histories of patients' physiological data. The server unit provides the required communication network while the personal computer unit may be used as an access station from which the status of patients can be monitored, past histories retrieved and physiological parameter threshold values for individual patients set.

The personal computer unit is adapted such that a computer program matches each time-coded data packet to the measuring device it originated from (thereby to the patient). Furthermore, the control unit, through the unique receiver identifier appended to the data packet, is able to track the location from which said data packet was transmitted from (thereby to the location of the patient during the measurement period). In addition, the approximate date and time at which the measurement was taken are also tracked via the appended time-code. The personal computer may also compare the measured value of the temperature of a patient against a preset threshold value of 37.5° C., for example. The monitoring program may be such that an audio-visual alert may be given should the temperature (or any other measured physiological parameter) exceed a preset threshold (or goes out of normal range).

The system may be linked to the Internet thereby allowing health specialists from other health facilities, especially those who are overseas, to monitor and retrieve data should they be authorized to do so.

A device, as used in the present invention, for measuring at least one physiological parameter includes an integrated switching device. The integrated switching device may be operated by a non-radio frequency switching activation signal generated by a switching activation device. The measuring device also comprises a measurement unit for measuring at least one physiological parameter, and a radio frequency signal transmitting device for transmitting a measured value of the at least one physiological parameter. In the device of the invention, the measurement unit and/or radio frequency signal transmitting device are/is activated if the integrated switching device is in a first switching status and deactivated if the integrated switching device is in a second switching status.

The switching activation device may be in the form of a magnetic activation switch that comprises at least one permanent- or electro-magnet that generates a magnetic field that is sufficiently strong to close the integrated switching device. In such an embodiment, the integrated switching device may be, but is not limited to, a magnetic relay switch, a reed switch, a momentary contact switch or any other variety of switch that is actuated by magnetic means. The magnetic activation switch causes the integrated switching device to reach the first switching status when the integrated switching device is placed within the magnetic field of the magnetic activation switch. The strength of the magnetic field may vary according to the size and the strength of the magnet used therein. In an exemplary embodiment of the switching activation device, the strength of the operating range of the magnetic field lies between 7-21 AT and the release range lies between 3-16 AT.

Other possible means of activating the measuring device include, but are not limited to, a mechanical actuator mechanism. The mechanical actuator mechanism may comprise a mechanical switch, which is situated in a recessed portion of the measuring device to prevent a patient from tampering with it. The mechanical actuator mechanism may also comprise a pin adapted to fit into the recessed portion and actuate the mechanical switch, for example. Accordingly, when the pin actuator actuates the mechanical switch, the integrated switching device will attain the first switching state. The mechanical switch may be, but is not limited to, a pressure switch, a contact switch, a slider switch, a rocker switch, a push-button switch and a rotary switch.

In the above-mentioned embodiment where a mechanical switch, such as a pin actuated mechanical switch, is used, the first actuation of the mechanical switch sets the measuring device into the first sub-status of the first switching status. The first sub-status of the first switching status is the initialization state and takes place during registration. Accordingly, as described above for this embodiment, during the initialization status of the first switching status the measuring device transmits registration packets periodically. Each registration packet contains the signal/data field, which contains the relevant data to indicate to the control unit that registration is taking place or is initiated. The control unit in turn will create an association between the measuring device being registered and a profile/person to which said measuring device would be attached to.

Subsequently, when the measuring device having the pin actuated mechanical switch is removed from the switching activation device, it then enters the "ON" sub-status of the first switching status and continues to transmit except that it now transmits information packets periodically to the control unit. Each information packet, as with the registration packet, contains the signal/data field. However, the signal/data field of the information packet now only includes data specific to the information transmission mode, and not to the registration mode or de-registration mode. In other words, the information now transmitted to the control unit pertains to the person to which the measuring device is attached to and may be relate to a physiological parameter such as the temperature, heart rate or pulse rate, for example.

When the mechanical switching measuring device, in the information transmission mode (or "ON" sub-status), is placed once again in contact with the pin of the switching activation device, it enters the de-initialization sub-status of the second switching status and begins to transmit de-registration packets periodically to the control unit. Each de-registration packet also contains the signal/data field, but in this case the field indicates the de-registration of the measuring device to the control unit. Finally, when de-registration is complete, the measuring device enters the "OFF" sub-status of the second switching status.

Further examples of mechanical activation may be selected from the group consisting of a pressure switch, a contact switch, a slider switch, a rocker switch, a pushbutton switch, and a rotary switch. Each mechanical switch may be adapted to allow for the four sub-statuses of the first and second switching statuses to be attained respectively.

The measuring device incorporates a radio frequency (RF) signal-transmitting device. The RF signal-transmitting device is adapted to provide for one-way radio frequency communication. However, if necessary, an embodiment that requires the monitoring system to communicate with the patient may utilize a two-way RF communication device. In this case, the RF signal-transmitting device provides a wireless two-way transfer of data and signals between the measuring device and the receiver unit.

In principle, the measurement unit of the measuring device may be adapted to measure any physiological parameter, such as the body temperature, blood pressure, pulse rate, $SpO_2$, blood $CO_2$ and $O_2$ levels, electrocardiogram (ECG), blood glucose levels and respiration rates or any combination thereof. It is to be understood that any other appropriate measuring device for measuring a physiological parameter may also be used.

In one embodiment, each measuring device may further include a unique identifier. The RF signal-transmitting device transmits the unique identifier to a monitoring system in order that the monitoring system may precisely identify the individual measuring devices present within the system and those from which data is being transmitted. Since each measuring device is worn by a patient, the personal particulars of each patient may then be also associated with the unique identifier of their respective measuring devices.

The measuring device is adapted such that upon being activated by the external switching activation device, the integrated switching device attains, as mentioned above, a first switching status. During the first switching status, the RF signal-transmitting device will transmit the said unique identifier to the monitoring system along with the physiological parameter value in order to aid in the calibration of the measuring device.

The switching activation device of the present invention may include at least one surface that acts as an activation portion. Generally, the activation portion may be either mechanical or magnetic in nature. The activation portion in one embodiment of the invention may comprise a two-tier recessed portion. The shape and size of the two-tier recessed portion is complementary to at least one surface of the measuring device. This allows the measuring device to fit into the recessed portion. When the measuring device is fitted into the recessed portion, it undergoes switching to either a first switching status or to a second switching status when the switching activation device is brought into contact with the at least one measuring device. The recessed portion may be of any shape. Exemplary shapes include circular shapes, rectangular shapes and polygonal shapes. Additionally any other irregular shape, that may be adapted to the shape of the body of a person, may be used. The fit may be a loose or tight fit depending on the application and the preference of a user.

As explained above, the integrated switching device of the measuring device can be activated via mechanical means. In one such embodiment the two-tier recessed portion may have the appropriate mechanical actuator within the recessed portion for switching the integrated switching mechanism into either a first switching status or to a second switching status. In another embodiment, the mechanical activation means may be located on the measuring device and may be activated when fitted into the recessed portion of the switching activation device.

In one embodiment wherein magnetic actuation means are utilized for switching the integrated switching device from a first to a second switching status, a magnetic field is generated either from or immediately beneath the recessed portion. The strength of the magnetic field should be sufficient enough to cause the integrated switching mechanism to switch from the first to a second switching status. If the magnetic field generated is sufficiently strong, locating the measuring device proximate to said switching activation device may also switch the integrated switching device from a first switching status to a second switching status.

In addition, the invention is directed to a method and switching activation device using the system as described above. This method comprises:

Activating the at least one measuring device by bringing the measuring device into contact with a switching activation device thereby causing the integrated switching mechanism of the at least one measuring device to undergo switching to a first switching status, α Registering the at least one measuring device through association of said measuring device to the particulars of a person in an initialization sub-status, Measuring at least one physiological parameter of the person using the measuring device in an "ON" sub-status, and a Monitoring the at least one measured physiological parameter of the person.

Activating the measuring device involves placing the measuring device in contact with the switching activation device. Upon coming into contact with said switching activation device, the integrated switching mechanism is activated and enters a first switching status thereupon; the radio frequency signal-transmitting device starts the transmission of a registration signal to the registration/control unit.

The registration process is conducted serially, meaning that one measuring device is registered at a time in a sequential manner. The registration signal is essentially a data packet comprising the unique identifier along with the battery status, a signal/data field indicating registration and a measured physiological value. The registration unit receives said registration signal and associates a person with said unique identifier of a measuring device. The particulars of a person may be keyed in manually to the registration unit or read from the bar code of a standard identification document such as a driving license or identification card, for example.

After the registration process, the measuring device starts to measure the required physiological parameter, such as the temperature, for example. In this embodiment where the temperature is measured, the measuring device may be attached to the person by means of at least one membrane. In the embodiment where the measuring unit is a thermometer, the measuring unit is attached to be in direct contact with the body of a patient. The portion of the measuring unit that is in contact with the body will measure the temperature of the patient accordingly. If the measuring device is placed for a prolonged period of time in direct contact with the body of a patient, sweat may accumulate around the area of the body that is in direct contact with the measuring device. As this may lead to hygiene issues such as rashes and unpleasant odors, the measuring device may be sandwiched between a first adhesive membrane that is directly adhered to the body and a second adhesive membrane. The second adhesive membrane secures the measuring device to the first membrane and encloses the measuring device between the first and second membranes.

An example of such a membrane that may be used is Tegaderm™ manufactured by 3M Heath Care. In this respect, it should however be noted that any transparent, semi-permeable or permeable membrane may be used provided that the thermal properties of the membrane in use do not adversely affect the measurement of the required physiological parameter.

After registration, the measuring device proceeds to measure the assigned physiological parameter intermittently. When measuring the temperature of a patient, the measuring device obtains the necessary value and transmits, intermittently, the measured value to the receiver unit in the form of data packets, for example. Along with the measured value, the unique identifier and the battery status of the measuring device are also included in each data packet transmitted to the receiver unit. As mentioned above, the transmission of the data packets is conducted according to the time-slot allocated by the anti-collision algorithm used by the measuring device. The receiver unit receives the data packet and appends the unique receiver identifier to every data packet received. In addition, each receiver unit appends a time-code comprising of the time and date of receipt of a particular data packet. The receiver forwards each received data packet to the control unit for recordation and monitoring.

The control unit is used to compare the measured value of at least one physiological parameter with a predetermined threshold value. An exemplary method of calculating said predetermined threshold value that can be used here is disclosed in PCT application WO 2005/006970 A1. Through the use of a graphic user interface (GUI) and a suitable multimedia system, the control unit may be able to provide audio and visual alerts and information-on-demand. The audio and visual alerts may be configured to be activated should the measured physiological values deviate by a predetermined percentage or value from the predetermined threshold values obtained from the method disclosed in the above-mentioned PCT application.

The accompanying drawings mentioned hereafter, and the detailed explanations that follow, will serve as an illustration to better aid in the understanding of the various non-limiting embodiments of the present invention.

FIG. 11 illustrates a further embodiment of the switching activation device of the system.

Figure 1:
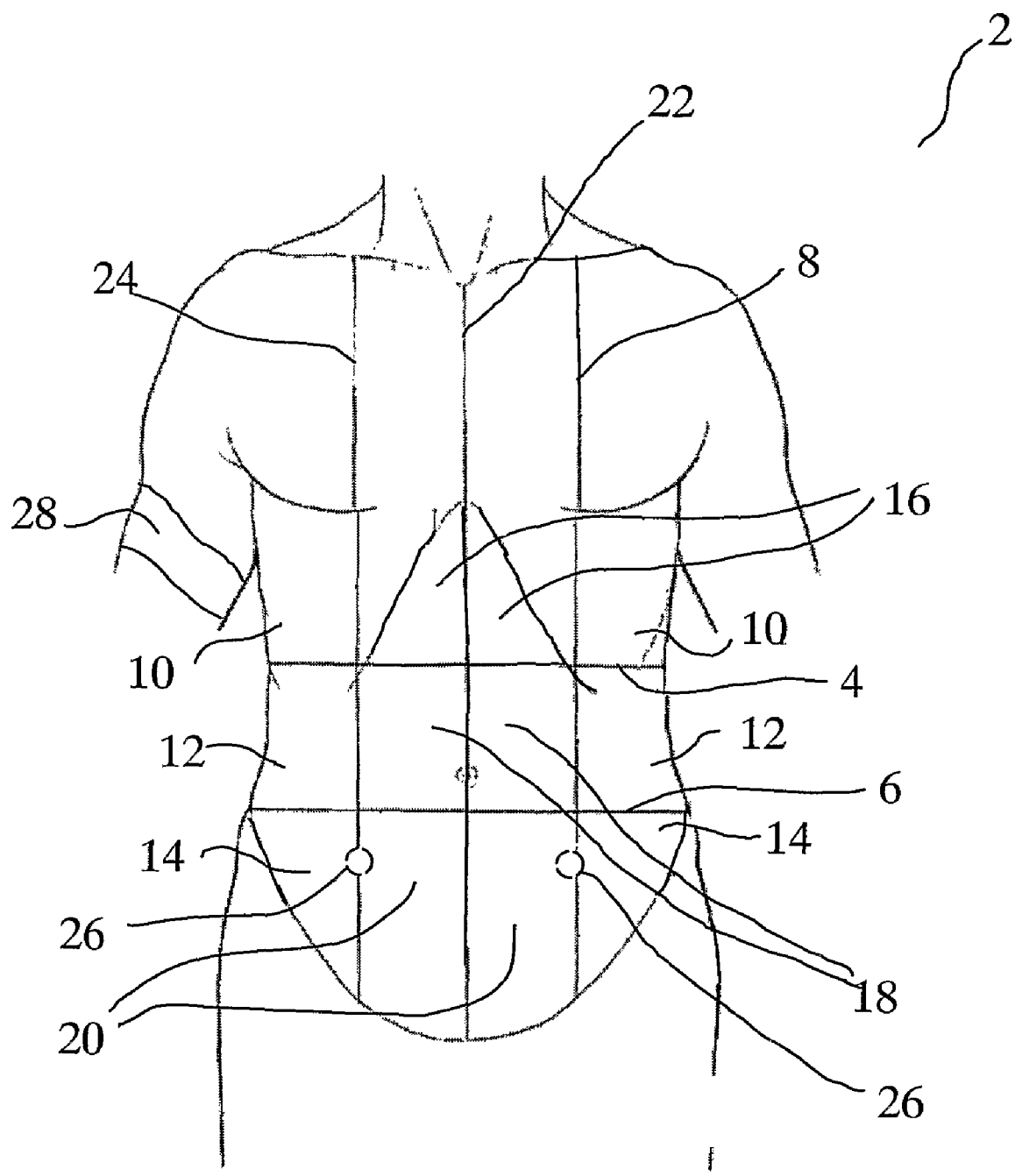
FIG. 1 is an illustration of a human torso from the frontal view.

FIG. 1 illustrates the anatomy of the human torso. The abdomen is divided into three zones and nine regions, by imaginary planes, two horizontal and three lateral planes. The edges of the horizontal planes being indicated by lines 4 (Transpyloric plane) and 6 (Transtubercular plane) and the edges of the lateral planes being indicates by lines 8 (left lateral plane), 24 (right lateral plane) and 22 (centre dividing plane) drawn on the surface of the body. The breakdown of the division of the abdomen into the 3 zones and 9 regions are as follows:

The middle region of the upper zone is called the epigastric 16, and the two lateral regions the right and left hypochondriac 10. The central region of the middle zone is the umbilical 18, and the two lateral regions the right and left lumbar 12. The middle region of the lower zone is the hypogastric or pubic 20, and the laterals are the right and left iliac or inguinal 14. The middle regions, viz., epigastric, umbilical, and pubic, can each be divided into right and left portions by the centre dividing line 22.

In the one embodiment, the measuring device 26 of the present invention is placed on the middle region located between the right iliac 14 and the right hypochondriac 20 or between the left iliac 14 and the left hypochondriac 20, preferably along the line 24 or line 8 respectively for optimum results. To ensure that the measuring unit of the of the measuring device 26 is in optimum contact (an acceptable area of contact) with the skin of the patient, two layers of adhesive are used to help negate the slipping effect that may be present due to the perspiration from the skin of a patient. In another preferred embodiment, the measuring device 28 may be wrapped around the cuff of the patient as shown in FIG. 1.

Figure 2:
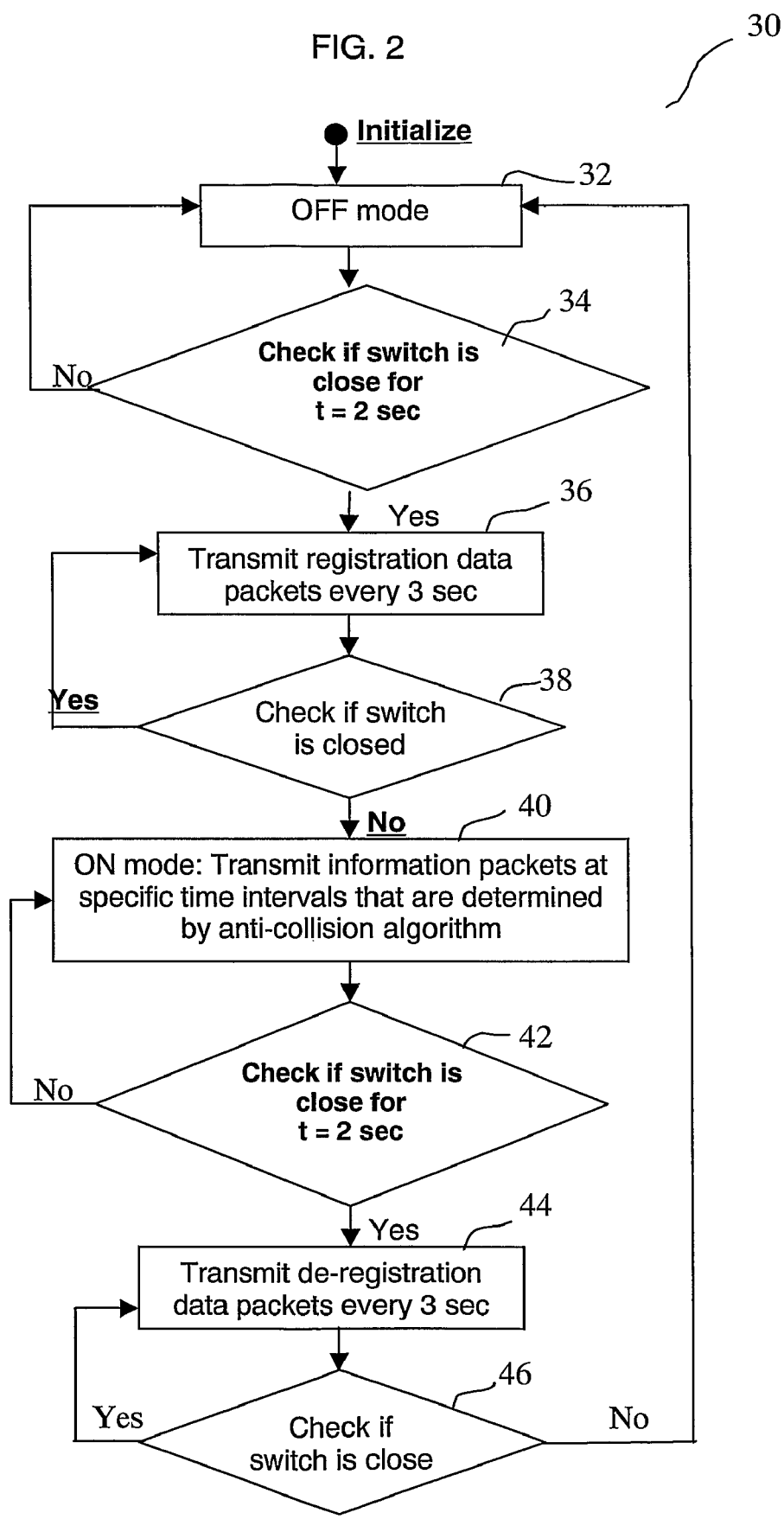
FIG. 2 illustrates the flow chart for the program, called the measuring device control program (MDCP) hereafter, which in one exemplary embodiment controls the operation of the measuring device.

FIG. 2 illustrates the flow chart for the program, called the measuring device control program (MDCP) 30 hereafter, which controls the operation of the measuring device 26 or 28. After initialization (power up of the measuring device 26 or 28), the MDCP drives the measuring device 26 or 28 into the "Off mode 32. Next the MDCP runs a check 34 to establish if the magnetic switch, referred to as switch in the flow chart, has been closed for a period 't', said period 't' being of at least two seconds. When the switch has been closed for two seconds, the MDCP initiates the transmission of registration packets (initialization sub-status of the first switching status) at three-second intervals 36 by the measuring device 26 or 28. Otherwise, the MDCP loops back to the previous step 32. In the transmission of a registration packet step 36, the MDCP continues to monitor the state of the switch 38. The registration packet comprises the unique identifier of the measuring device, a signal/data field to indicate registration, the battery status of the at least one measuring device and at least one measured physiological parameter value.

The registration packet includes the signal/data field to indicate to the control system that registration of the measuring device is taking place. This feature ensures that the registration unit, which may also receive data packets transmitted by other measuring devices in the vicinity, registers each measuring device in a serial manner. To do so, only one measuring device sits in the switching activation device during the activation sequence.

In the event that the switch is open, the MDCP drives the measuring device 26 or 28 into the "ON" mode 40 (second sub-status of the first switching status). Failing which, it loops back to the previous step 36 and the measuring device 26 or 28 continues to send out registration packets at three-second intervals. In the "ON" mode 40 the MDCP calls the anti-collision algorithm (ACA) to generate pseudo-random time intervals Ts. The program drives the measuring device 26 or 28 to transmit information packets (viz. temperature, blood pressure etc.) at these pseudo-random time intervals. The ACA generates each pseudo-random time interval T so that the probability for two or more measuring devices 26 or 28 to transmit packets simultaneously is reduced.

In the "ON" mode 40, the MDCP will monitor the state of the switch 42 to establish if it has been closed for a period 't' of two seconds. Otherwise, the MDCP loops back to the previous step 40 and continues to drive the measuring device 26 or 28 to transmit the aforementioned information packets. Then the MDCP drives the measuring device 26 or 28 to transmit the data de-registration packets at 3 second intervals and stop the transmission of information packets 44 (first switching sub-status of the second switching status). The de-registration packet comprises the unique identifier of the measuring device, a signal/data field to indicate de-registration, the battery status of the at least one measuring device and at least one measured physiological parameter value.

From this step 44 the MDCP continues to check the status of the switch 46. As long as the switch remains closed it continues transmitting de-registration packets. The moment it detects that the switch is open, it loops back to the very beginning 30, viz. the step where it is in the "OFF" mode 30 (second switching sub-status of the second switching status). From here, the whole cycle repeats again.

Figure 3:
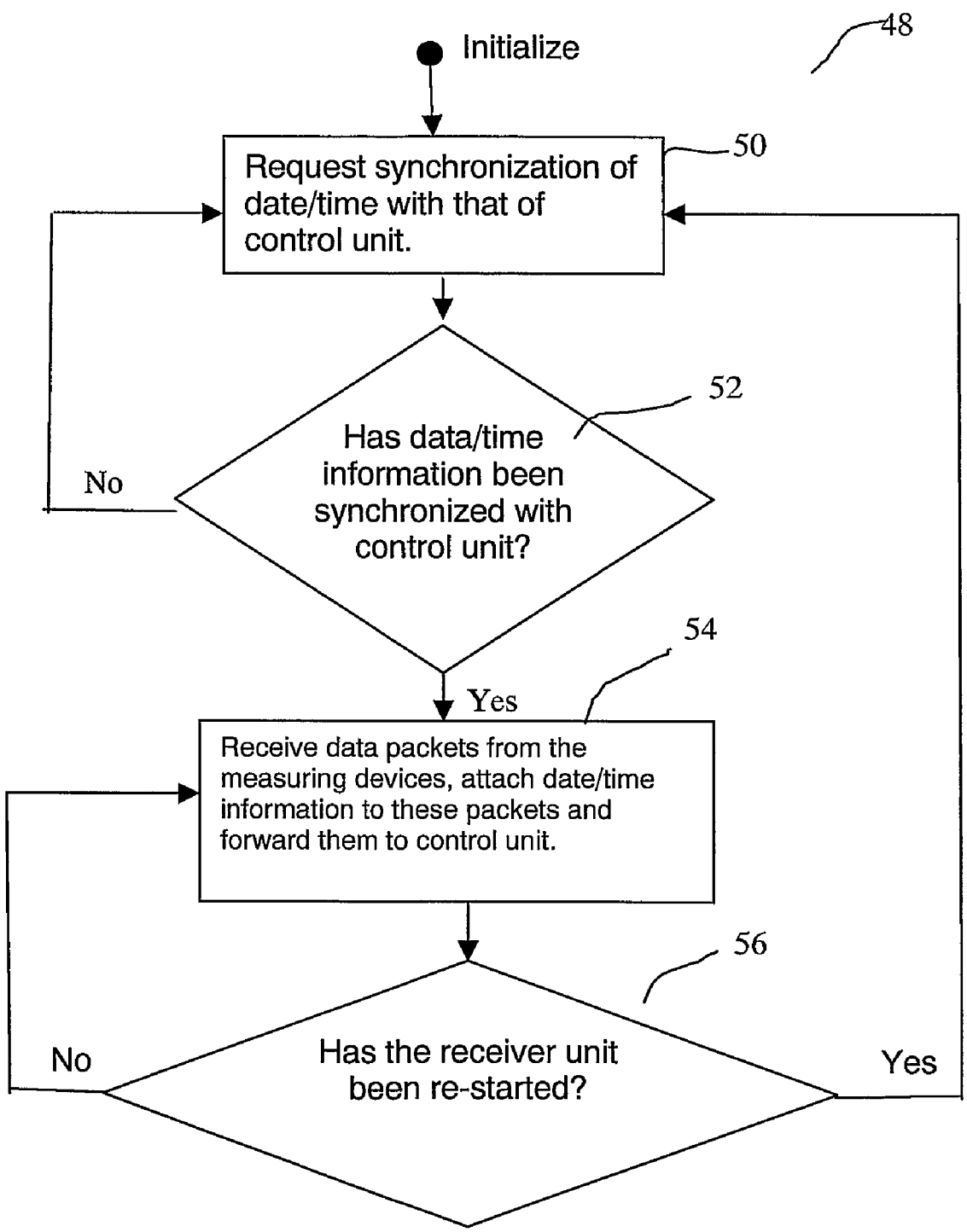
FIG. 3 illustrates the flow chart for one exemplary program controlling the synchronization of the date/time of the receiver unit with the control unit.

FIG. 3 illustrates the flow chart for the program controlling the synchronization of the date/time of the receiver unit with the control unit. This program is termed the Synchronization Date/Time Program or (SDTP) 48. Upon initialization (power up of the system), the SDPT 48 drives the receiver unit (RU) to request for synchronization of date/time with the control unit 50. Next, the SDPT 48 checks if the date/time of the RU has been updated after the request was sent 52. Otherwise, the SDPT 48 continues to drive the RU to send the aforementioned synchronization request 50. If the date/time of the RU has been updated, the RU can proceed to receive packets from the measuring devices, date/time stamp these data packets and forward them to the control unit 54. The SDPT 48 also checks if the RU has been re-started 56. If it has, then the SDPT 48 loops back to the first step 50 and send out the request for synchronization as mentioned. The whole process is then repeated.

Figure 4:
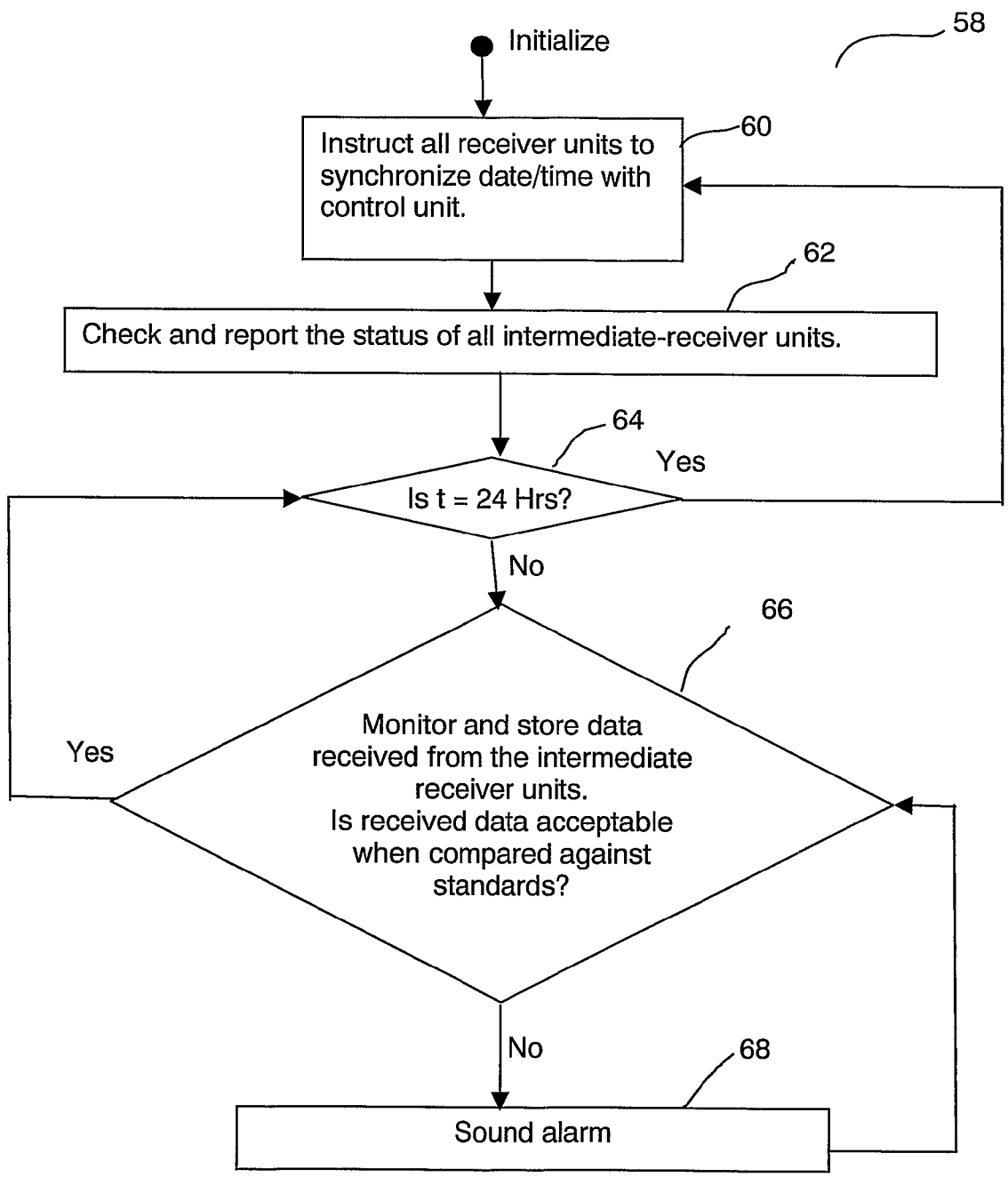
FIG. 4 illustrates one program that controls the operation of the control unit (CU)

FIG. 4 illustrates the control unit program (CUP). The program sends instructions to all RUs, upon initialization (power up of the system), to synchronize their date/time with the control unit (CU) itself 60. Next, the CUP checks and reports on the status of all RU 62. This is done to ensure that all RU are functioning and to ensure that their data/time are all synchronized with the CU. The CUP also checks if the duration t, measured from the time of initialization till the current time, is 24 hours 64. If t is 24 hours, CUP loops back to the first step 60 and retransmit the synchronization instructions to all RUs. If not, CUP monitors and stores data received from the RUs 66. CUP compares the data received from the RUs with the standards and determines the acceptability 66. If data received is not acceptable, CUP sounds an alarm 68. It will continue to assess the acceptability of the data received in comparison to the standards. The CUP will stop the alarm only when the data received is acceptable.

Figure 5:
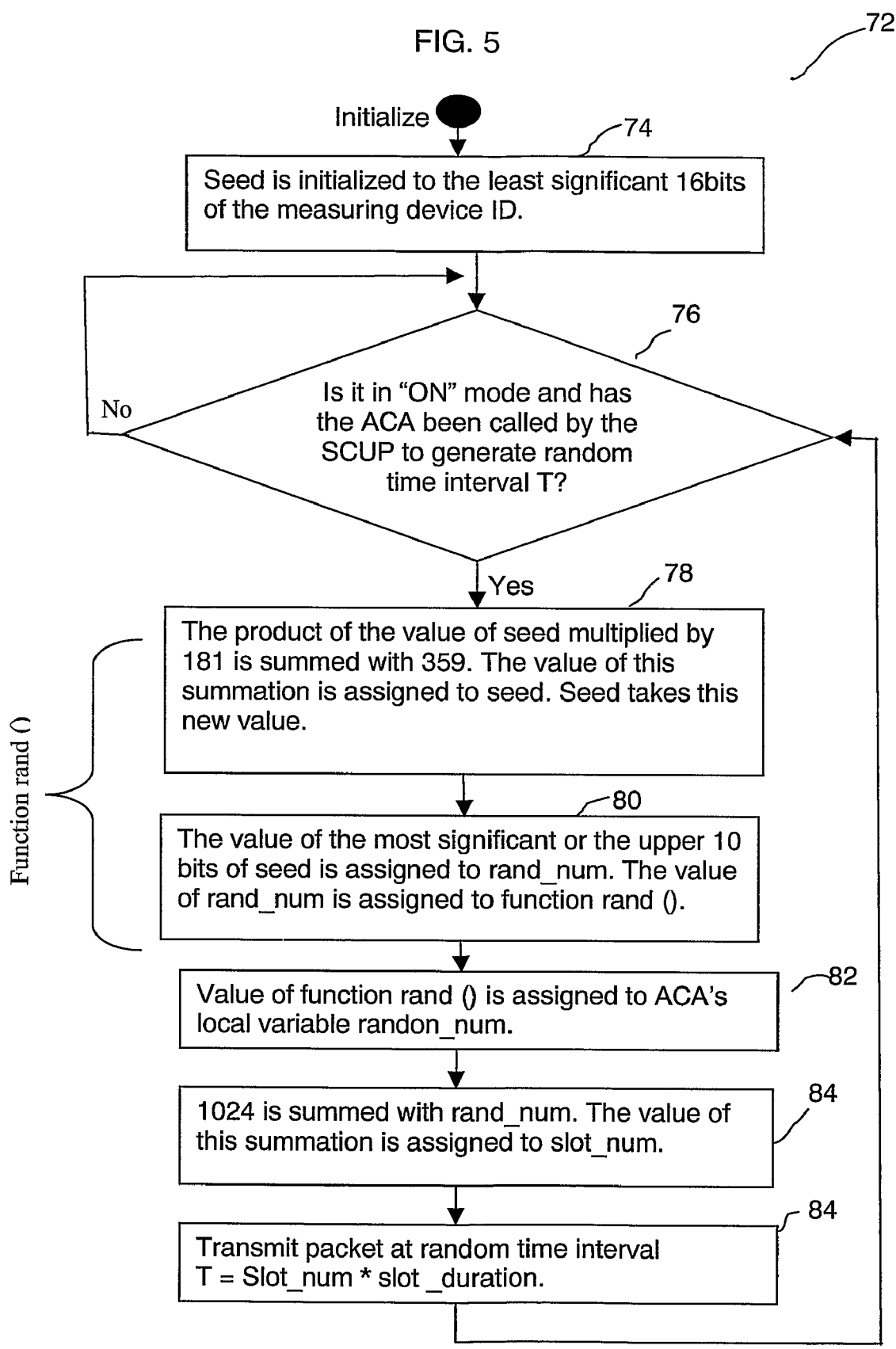
FIG. 5 shows the flow chart of the anti-collision algorithm (ACA) according to one embodiment of the invention.

FIG. 5 shows the flow chart of the Anti-collision algorithm (ACA) 72. Upon initialization (power up) of the measuring device 26 or 28, 'seed' (a global variable) is initialized to the least significant 16 bits of the measuring device ID 74. Note that 'seed' (a global variable) can be "seen" by all programs running within the measuring device 26 or 28 (viz. ACA 72, MDCP 30, function rand ( ) etc.). The ACA 72 checks if the measuring device 26 or 28 is in the "ON" mode and if the MDCP 30 has called for it to generate the pseudo-random time interval T 76. If not, the ACA 72 loops back to the previous step 76 and continues this check. If yes, the ACA 72 will call the function 'rand ( )'. In the function 'rand ( )', the product of the value of 'seed' (global variable) multiplied by 181 is summed with 359 78. The resultant value of this summation is limited to the range 0 to 65535 by ignoring overflow, and is then assigned to 'seed' (global variable) 78. Hence 'seed' (global variable) takes this new value thereafter. Next, the value of most significant or upper 10 bits of the seed (a 16 bit value) is assigned to the local variable 'rand_num' 80. The value of 'rand_num' is then assigned to the function 'rand ( )' 80. Note that each time the function 'rand ( )' is called by the ACA 72, the global variable 'seed' will be updated (changed).

Next, the ACA 72 proceeds to assign the value of the function rand ( ) to its own local variable also called random_num 82. The value 1024 is then summed with the value of random_num 84. The value of this summation is assigned to slot_num (local variable of ACA) 84. Finally, the pseudo-random time interval T is calculated as the product of the value of slot_num and the value of the slot_duration (time of each slot). A packet will then be transmitted by the measuring device 26 or 28 at a time equal to T calculated from the current time. Note that the transmission time line is divided into time slots. In the preferred embodiment, the time slots are each 100 ms.

Once a packet has been transmitted, the ACA 72 loops back to the step where it checks if the measuring device is in the "ON" mode and if the MDCP 30 has called for it to generate the pseudo-random time interval T 76. If the measuring device is in the "ON" mode and if the MDCP 30 has called for it to generate the pseudo-random time interval T, the same cycle is repeated to calculate the next pseudo-random time interval T for the transmission of the next packet.

Figure 6:
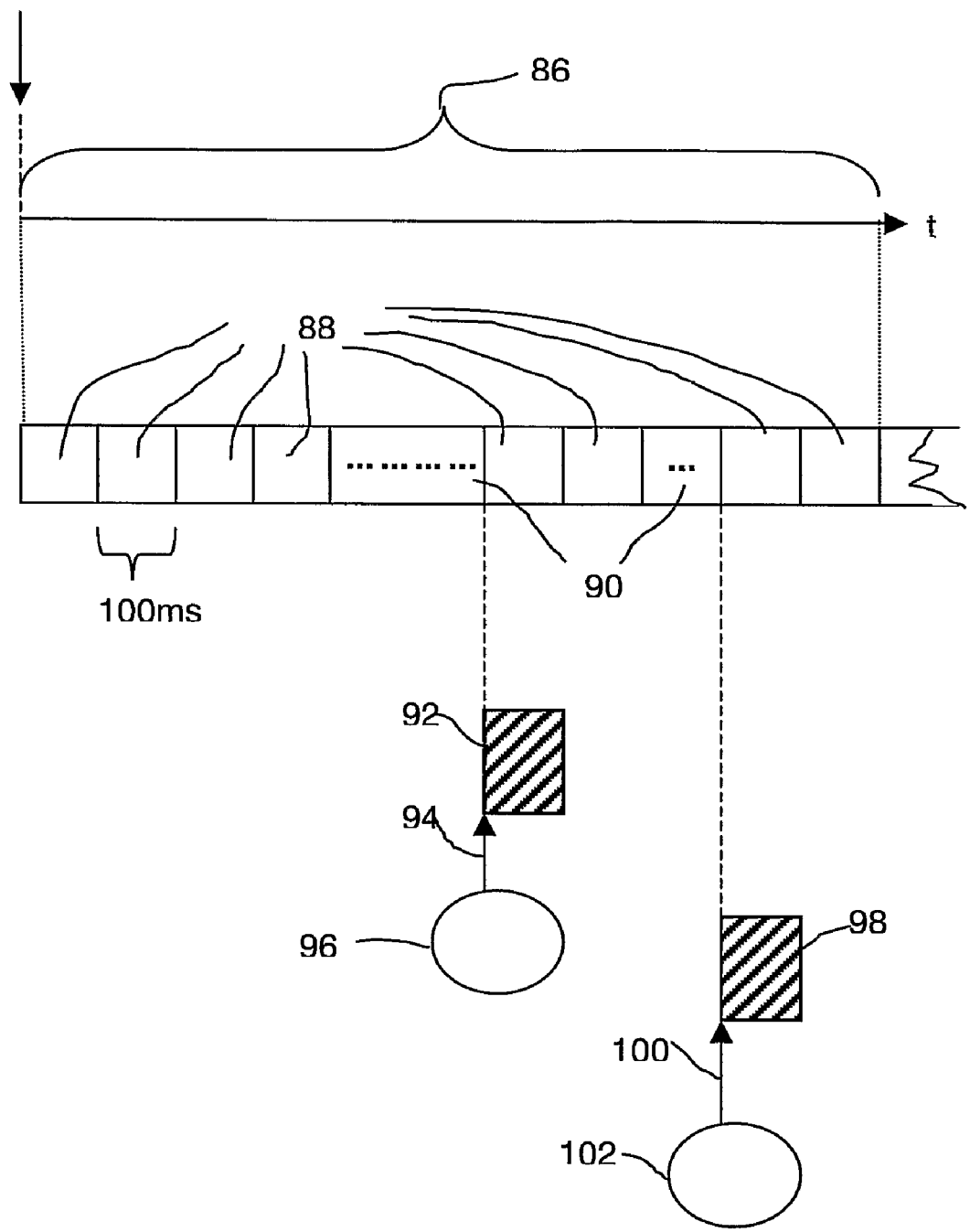
FIG. 6 illustrates the transmission time line as well as the different transmission times of the measuring devices in one embodiment.

FIG. 6 illustrates the transmission time line 86 as well as the different transmission times of the measuring devices in the preferred embodiment. For convenience, only two different measuring devices are shown. The transmission time line 86 is divided into time slots of 100 ms each 88. The doted time slots 90 represent several 100 ms time slots. The two different measuring devices 96 and 102 transmit data packets 92 and 98 respectively. Measuring device 96 transmits a data packet 92 at the start of the time slot pointed out by the arrow 94. While measuring device 102 transmits its data packet 98 at the start of a different time slot pointed out by arrow 100. The high probability of transmission of data packets at different time slots is made possible with the use of the ACA.

The ACA generates the pseudo-random time interval T, wherein T equals the multiplication of the slot_num and the slot_duration. The slot_duration equals the slot time, i.e. 100 ms. The slot_num generated is pseudo-randomized. The pseudo-randomized nature of T allows for the high probability of transmission of data packets at different times for the different measuring devices in the system. For example, the slot_num for the measuring device 96 is 1024 and the slot_num for the measuring device 102 is 2000. Measuring device 96 commences transmission of its data packet 92 at the start of the 1024$^{th}$ time slot and measuring device 102 will begin transmitting its data packet at the 2000$^{th}$ time slot. The ACA thus reduces the probability of collision between the data packets sent out by each individual measuring device through the use of a pseudo-randomized scheme for the time of transmission of data packets.

Figure 7:
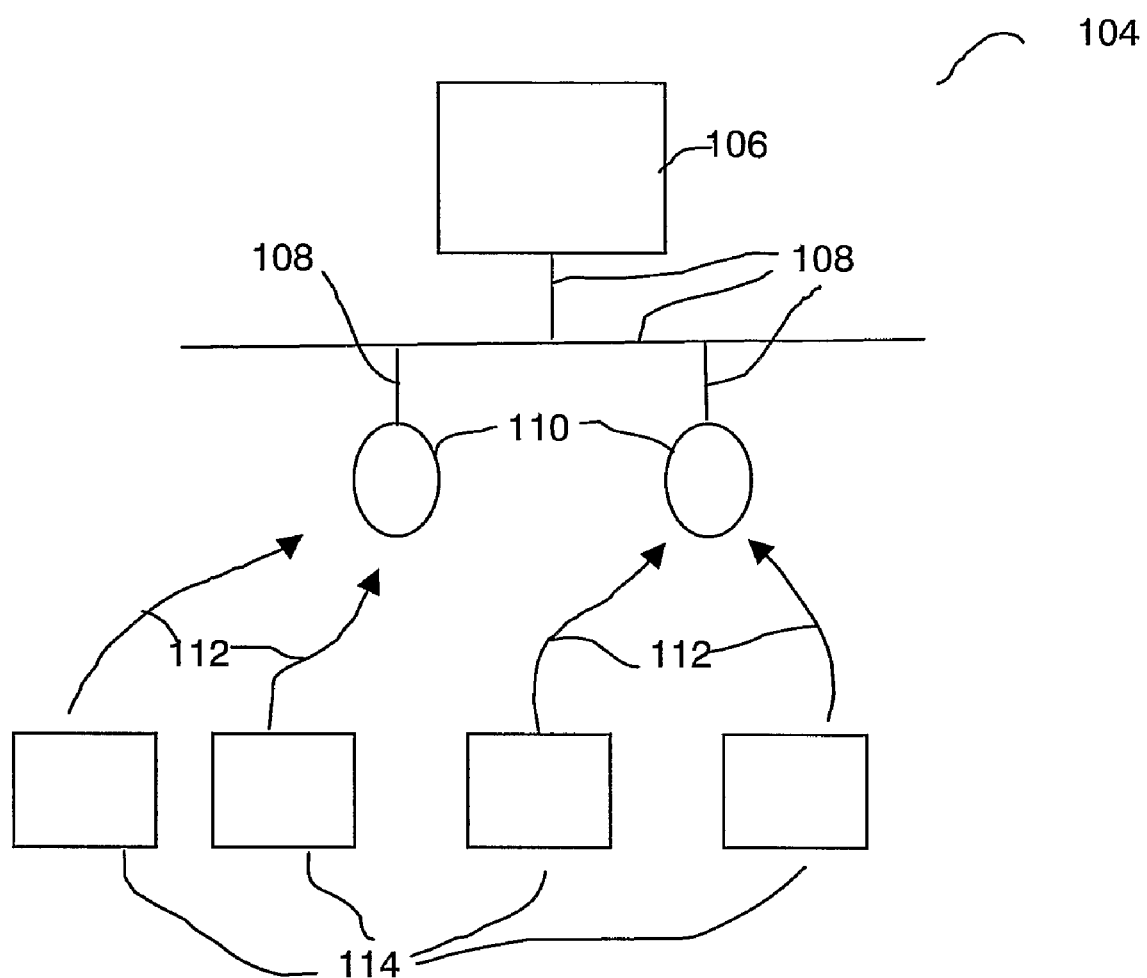
FIG. 7 illustrates the system configuration of one embodiment indicating the various components and how they are connected to each another.

FIG. 7 illustrates the system configuration showing the components and how 25 they are connected to one another 104. The components of the system comprise: measuring devices 114, intermediate receiver nodes (RU) 110 and the control unit 106. For convenience, only four measuring devices 114 and two RUs 110 are shown. It is to be understood by those skilled in the art that the number and combination of the measuring devices and RUs can be varied. Also, the control unit 106 can comprise a number of PCs and/or servers which are either wirelessly and/or hardwired together in a Local Area Network (LAN). The RUs 110 are connected to the control unit 106 either wirelessly and/or hardwired.

In one preferred embodiment, the RUs 110 are connected to the control unit 106 via the RS485 serial communicator 108. The measuring devices 114 are wirelessly connected to the RUs 110. The wireless connection only allows for one-way communication, i.e. only from the measuring devices 114 to the RUs 110 as depicted by the direction of the arrows 112.

The measuring devices 114 comprise a collection of different measuring units, each for measuring different bio-data such as blood pressure, pulse rate, respiration rate, temperature, SpO$_2$, ECG, etc. in one preferred embodiment. Each of the measuring devices 114 may comprise sensing devices to sense various types of bio-data, viz. blood pressure, pulse rate, respiration rate, temperature, SpO$_2$, ECG, etc. in another preferred embodiment.

Figure 8:
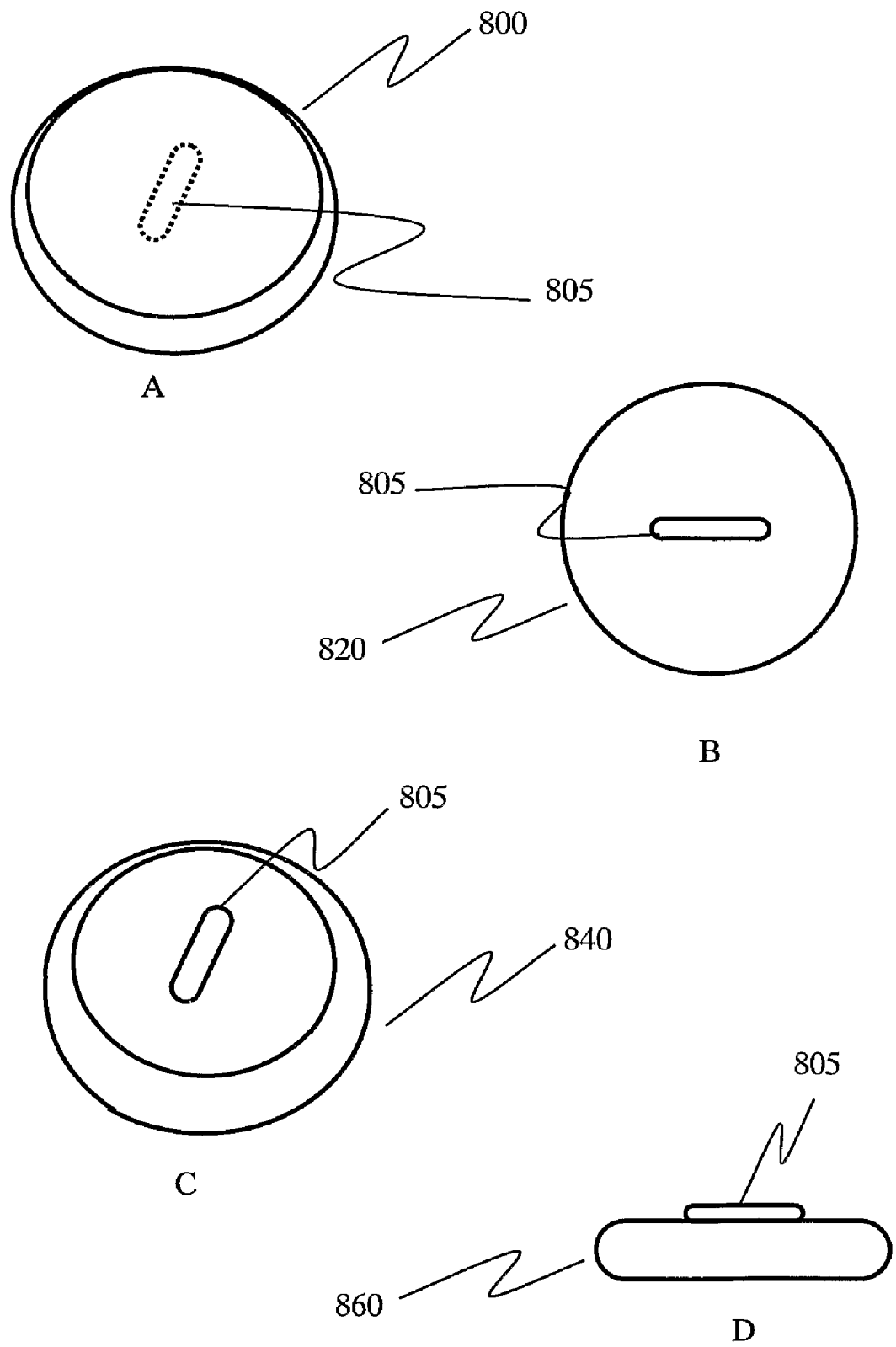
FIG. 8 illustrates an embodiment of the measuring device component of the system.

FIG. 8A shows a measuring device 800 from a top view. Portion 805 of the measuring device of the present embodiment acts as a contact point between the measuring device 800 and the switching activation device. The measuring device may contain therein a mechanical or a magnetic relay switch that may be actuated by magnetic means. That is, when in the presence of a magnetic field of sufficient strength, the mechanical or magnetic relay switch in the measuring device 800 is sent into a first switching state during which said measuring device 800 registers with the control unit (CU). FIGS. 8B-8D illustrate the measuring device from views 820, 840 and 860 respectively. In each of the said views, the portion 805 is visible. In view 860, the protruding of portion 805 from the main body of the measuring device 800 is clearly illustrated.

The placement of the measuring device 800 in contact with a magnetic field of a particular strength ensures that the activation or deactivation of the measuring device 800 takes place. Said activation or deactivation occurs via actuation of the mechanical or magnetic relay switch, for example. After the registration process, as described above, is complete, the measuring 800 device resumes normal functioning in that it measures and transmits, periodically, a value of the physiological parameter that it caters to along with any other suitable data such as signal strength, battery strength and unique identification signatures, for example.

After the measuring device 800 has completed the required physiological measurement tasks, it may require deactivation. In this respect, it is placed back into proximate range of a suitable magnetic field, such as that generated by a switching activation device 900 described hereafter for example. In the magnetic field, an active measuring device enters a second switching state during which it transmits a deregistration signal to the CU and subsequently, switches off completely.

Figure 9:
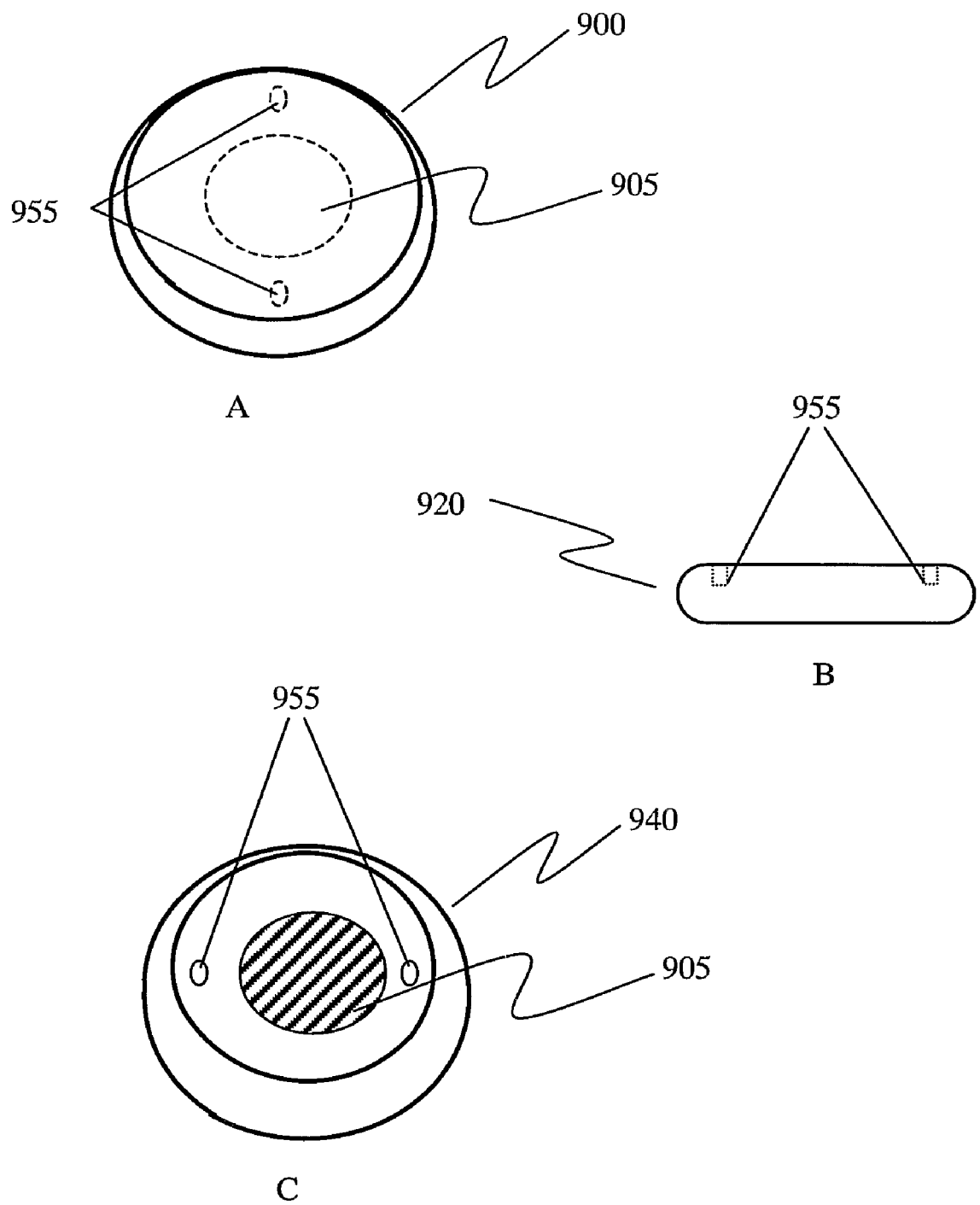
FIG. 9 illustrates a further embodiment of the measuring device component of the system.

FIG. 9 is an illustration of a further embodiment of the measuring device 900. The views 920 and 940 show that unlike the embodiment of FIG. 8, the present embodiment does not have a protruding portion 805. Instead, the shaded region 905 is flat and coplanar with the surface of the measuring device. The embodiment of FIG. 9 functions in the same manner, as that of FIG. 8 with the exception that the corresponding switching activation device need not have a complementary recess. Instead, as shown in FIG. 10, said switching device may simply have a corresponding flat planar surface on which the measuring device of FIG. 9 may be place for activation.

In a further embodiment of the measuring device of FIG. 9, a securing means may be incorporated thereto. The securing means may take the form of a socket and plug, for example. In this regard, the plug may be situated on the switching activation device 1000, such as that from FIG. 10, and the socket 955, formed on the measuring device 900 as shown. It should be noted that the location of the socket 955 and the corresponding plug 1055 may be reversed to be situated on the switching activating device and the measuring device respectively.

Figure 10:
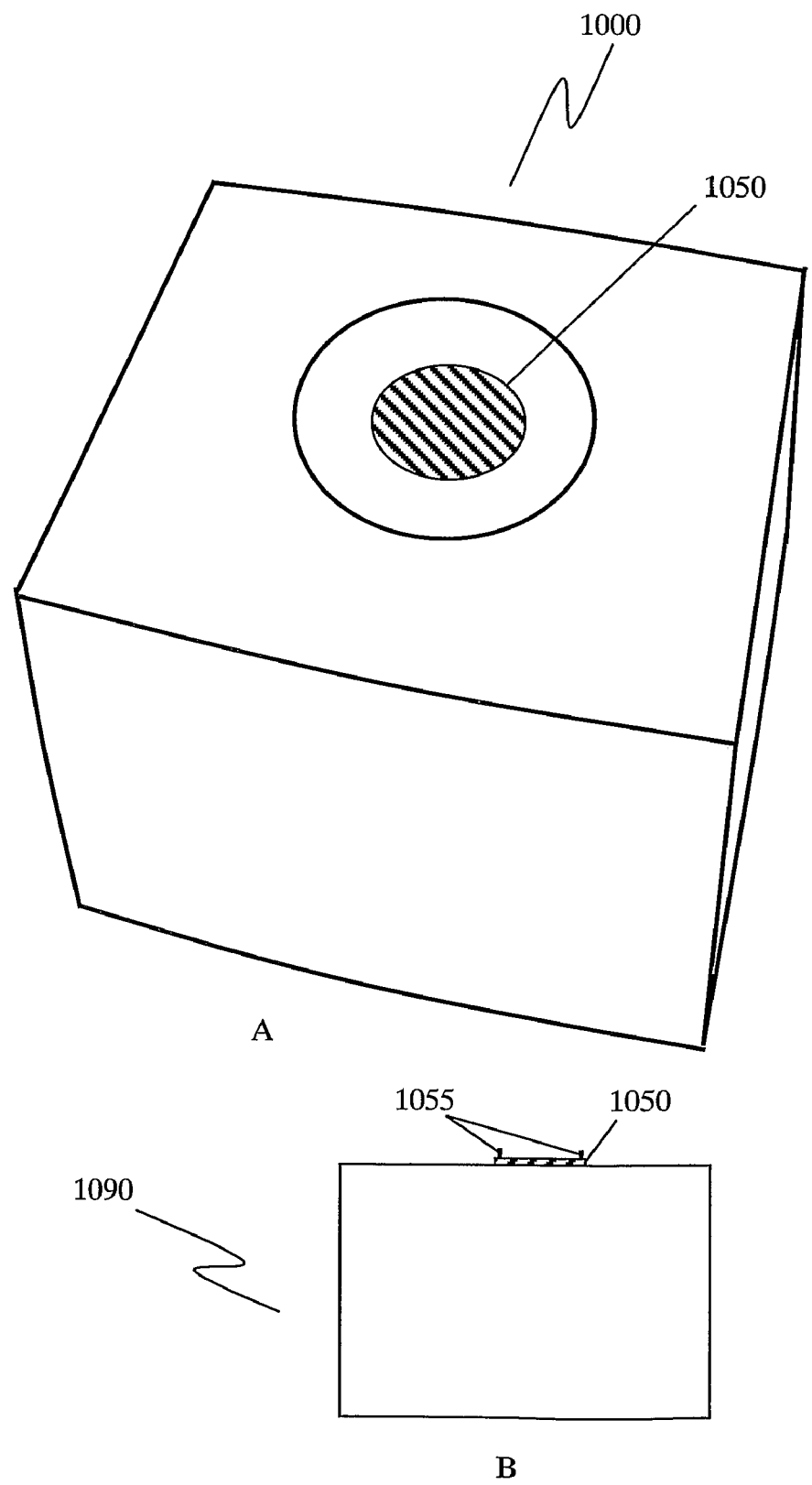
FIG. 10 illustrates an embodiment of the switching activation device of the system.

The embodiment of the switching activation device in FIG. 10 includes a flat activation portion 1050 upon which the measuring device 900 is placed. Accordingly, the switching to a first or second switching status takes place when the measuring device 900 is placed on the activating portion 1050. In an alternative embodiment of the activation portion 1050 of FIG. 10, may include plugs 1055 along the periphery of the activation portion 1050. In this embodiment, the measuring device 900 shown in FIG. 9, for example, may include corresponding sockets 955 to which the said plugs 1055 connect to thereby securing the measuring device b to the activation portion 1050. FIG. 10B illustrates a cross-sectional view 1090 of the switching activation device b and clearly shows the flat planar activation portion 1050.

The switching activation device 1100, such as one mentioned above is capable of providing a magnetic field capable of activating and deactivating the measuring device 800. FIG. 11 illustrates the switching activation device 1100 having magnetic actuation means. The switching activation device 1100 includes a first tier recess 1150 in which the measuring device 800 sits in during the registration sequence. The switching activation device 1100 also includes a second tier recess 1175 in which another portion of a measuring device 800 sits in. The shape of the measuring device 800 is complementary to the shape of the recess of the switching activation device 1100, like a socket and plug, for example. In addition, the switching device 1100 includes a pair of recesses 1180 located at opposite ends of the recess 1150. The recesses 1180 aid in the placement and removal of the measuring device 800 from the switching activation device 1100.

The switching activation device 1100 is placed in the recesses 1150 and 1175 and the magnetic field, closes the mechanical or magnetic relay switch. The magnetic field generated may be generated by an electromagnet (not shown) or a permanent magnet (not shown), for example. FIG. 11B illustrates a cross-sectional view 1190 of the switching activation device 1100 and clearly shows the two-tier recessed portion comprising first recess 1150 and second recess 1175.

It is to be noted that the present invention is by no means limited to the above-mentioned illustrated embodiments alone. The illustrated embodiments merely serve as exemplary embodiments to facilitate the understanding of and to better illustrate the working principles behind the present invention.

The invention claimed is:

1. A system for measuring at least one physiological parameter of at least one person comprising:
a switching activation device, and
at least one measuring device that measures the at least one physiological parameter,
wherein the switching activation device is designed such that when brought into contact with the at least one measuring device, the at least one measuring device undergoes switching to either one of two sub-statuses of a first switching status or to either one of two sub-statuses of a second switching status, wherein the two sub-statuses of the first switching status are an initialization sub-status and an "ON" sub-status respectively,
wherein the two sub-statuses of the second switching status are a de-initialization sub-status and an "OFF" sub-status respectively,
and wherein the at least one measuring device comprises
an integrated switching mechanism, and
a radio frequency signal transmitting device for transmitting a measured value of the at least one physiological parameter,
wherein the radio frequency signal transmitting device is activated if the integrated switching mechanism is in a first switching status and deactivated if the integrated switching mechanism is in a second switching status, said switching status being controlled by the switching activation device.

2. The system according to claim 1, wherein the integrated switching mechanism is operable by a non-radio frequency switching activator provided by the switching activation device.

3. The system according to claim 2, wherein the non-radio switching activator is selected from mechanical and/or magnetic activators.

4. The system according to claim 3, wherein the mechanical activator is selected from the group consisting of a pressure switch, a contact switch, a slider switch, a rocker switch, a push-button switch and a rotary switch.

5. The system according to claim 3, wherein the magnetic activator is selected from the group consisting of a magnetic relay switch, a reed switch and a momentary contact switch.

6. The system according to claim 1, further comprising at least one registration unit adapted to function in unison with the switching activation device, wherein said registration unit is a microprocessor capable of registering or deregistering the measuring device when said measuring device is in either the first or second switching state respectively.

7. The system according to claim 6, wherein the registration unit is adapted to recognize and record an association between the unique identifier of a measuring device and the particulars of a person during a registration process.

8. The system according to claim 1, further comprising at least one receiver unit wherein the at least one receiver unit is adapted to receive a data packet transmitted by the at least one measuring device.

9. The system according to claim 8, further comprising at least one controller unit wherein the at least one controller unit is adapted to receive a data packet from the at least one receiver unit.

10. The system according to claim 9, wherein the at least one controller unit is adapted to function as the registration unit.

11. The system according to claim 9, wherein the at least one measuring device, receiver, and controller unit are in communication with each other via a frequency communication network.

12. The system according to claim 9, wherein the at least one controller unit comprises an internal clock to provide for a date-time stamp (time-code).

13. The system according to claim 9, wherein the controller unit comprises:
at least one database storage and retrieval system
at least one server unit wherein said server unit provides for the frequency communication network and
at least one personal monitoring unit wherein said personal monitoring unit includes a graphic interface and audio system to provide visual and audio output signals.

14. The system according to claim 9, wherein the radio frequency signal transmitting device, receiver and controller unit are compatible with 802.1x wireless standard.

15. The system according to claim 8, wherein the data packet transmitted by the measuring device to the receiver comprises:
the unique identifier of the at least one measuring device,
a signal/data field and
at least one measured physiological parameter value.

16. The system according to claim 15, wherein the signal/data field comprises registration data, patient information data and/or deregistration data.

17. The system according to claim 15, wherein the data packet transmitted by the measuring device further includes a battery status of the at least one measuring device.

18. The system according to claim 8, wherein the at least one receiver comprises an internal clock to provide for a date-time stamp (time-code).

19. The system according to claim 18, wherein the at least one receiver is adapted to conduct an internal clock self-synchronization step with the internal clock of the control unit, after being reset or upon receiving an instruction to do the same.

20. The system according to claim 8, wherein each of the at least one receiver has stored therein a receiver unique identifier for identifying the at least one receiver unit to the at least one control unit.

21. The system according to claim 1, wherein the at least one measuring device has stored therein a unique identifier for identifying the at least one measuring device to the at least one registration unit or to the at least one controller unit.

22. The system according to claim 1, wherein the measuring device is adapted to use an anti-collision algorithm to provide, for each measuring device, a pseudo-randomized time-slot to periodically transmit each data packet.

23. A method of measuring at least one physiological parameter of a person using the system as defined in claim 1, said method comprising:
activating at least one measuring device by bringing the measuring device into contact with a switching activation device thereby causing the integrated switching mechanism of the at least one measuring device to undergo switching to a first switching status,
registering the at least one measuring device, measuring at least one physiological parameter of the person using the measuring device, and
monitoring, by comparing the at least one measured physiological parameter of the person with a predetermined value.

24. The method according to claim 23, wherein activating the at least one measuring device comprises placing the at least one measuring device in contact with a switching activation device, transmitting a unique identifier of the at least one measuring device to a registration unit after the measuring device receives the non-radio frequency activation signal and undergoes switching to a first switching status.

25. The method according to claim 23, wherein registering the at least one measuring device comprises transmitting the unique identifier of each of the at least one measuring devices to a registration unit serially, and registering the unique identifier of each of the at least one measuring devices serially.

26. The method according to claim 23, wherein de-registering the at least one measuring device comprises transmitting the unique identifier of each of the at least one measuring devices to the registration unit serially, and de-registering the unique identifier of the at least one measuring device serially after monitoring the at least one physiological parameter of the person by bringing the measuring device into contact with the switching activation device thereby causing the integrated switching mechanism of the at least one measuring device to undergo switching to a second switching status.

27. The method according to claim 23, wherein measuring at least one physiological parameter of the person comprises:

attaching the measuring unit is to the body of a person by at least one adhesive membrane, and transmitting a measured physiological value in a data packet to a controller unit during the registration process and periodically thereafter.

28. The method according to claim 23, wherein transmitting a measured physiological value from a measuring device to a receiver unit comprises:

utilizing an anti-collision algorithm when transmitting the data packet from the measuring device to a receiver unit to minimize the occurrence of data packet collisions when at least two measuring devices transmit said data packet simultaneously, using the receiver unit to receive the data packets from the measuring device, appending said receiver unique identifier to each data packet received by the receiver unit, appending a time and date of receipt information as a time-code to each data packet received by the receiver unit, and forwarding the time-coded data packet to the control unit for recording and monitoring.

29. The method according to claim 23, wherein monitoring the at least measured one physiological parameter of the person comprises using the control unit to compare the measured value of at least one physiological parameter with a predetermined threshold value, and using a graphic user interface, including an audio and visual alert, to determine if the measured value of the at least one physiological parameter deviates by a fixed percentage from the predetermined threshold values.

30. A measuring device for measuring at least one physiological parameter comprising:

a measurement unit for measuring at least one physiological parameter;

an integrated switching mechanism operable by a non-radio frequency switching activator provided by a switch activation device, wherein the switching activation device is designed such that when brought into contact with the at least one measuring device, the at least one measuring device undergoes switching to either one of two sub-statuses of a first switching status or to either one of two sub-statuses of a second switching status, wherein the two sub-statuses of the first switching status are an initialization sub-status and an "ON" sub-status respectively, wherein the two sub-statuses of the second switching status are a de-initialization sub-status and an "OFF" sub-status respectively, a radio frequency signal transmitting device for transmitting a measured value of the at least one physiological parameter, wherein the radio frequency signal transmitting device is activated if the integrated switching mechanism is in the first switching status and deactivated if the integrated switching mechanism is in the second switching status, said switching status being determined by the switch activation device.

31. The measuring device according to claim 30, wherein the integrated switching mechanism is operable by magnetic and/or mechanical activator.

32. The measuring device according to claim 31, wherein the integrated switching mechanism operable by magnetic activator is selected from the group consisting of a magnetic relay switch, a reed switch and a momentary contact switch.

33. The measuring device according to claim 31, wherein the integrated switching mechanism operable by mechanical activator is selected from the group consisting of a pressure switch, a contact switch, a slider switch, a rocker switch, a push-button switch and a rotary switch.

34. The measuring device according to claim 30, wherein the radio frequency signal-transmitting device is adapted to a one-way radio frequency communication.

35. The measuring device according to claim 30, wherein the measurement unit is a thermometer unit, a blood-pressure monitoring unit, an electrocardiogram (ECG) unit, a pulse rate measurement unit, a blood oxygen measurement unit, a blood gas measurement unit, a respiration monitoring unit or any combination thereof.

36. A switching activation device for switching the at least one measuring device that measures the at least one physiological parameter to either one of two sub-statuses of a first switching status or to either one of two sub-statuses of a second switching status, said switching activation device comprising:

at least one activation portion, wherein said activation portion, is complementary to at least one surface of the measuring device in shape and size such that the at least one measuring device undergoes switching to either one of two sub-statuses of the first switching status or to either one of two sub-statuses of the second switching status when the activation portion of the switching activation device is brought into contact with the at least one surface of the measuring device wherein the two sub-statuses of the first switching status are an initialization sub-status and an "ON" sub-status respectively, wherein the two sub-statuses of the second switching status are a de-initialization sub-status and an "OFF" sub-status respectively.

37. The switching activation device according to claim 36, wherein said activation portion is a two-tiered recessed portion that has a mechanical actuator situated within said recessed portion for switching the integrated switching mechanism of the measuring device into either the first or second switching status.

38. The switching activation device according to claim 36, wherein said activation portion generates a magnetic field sufficient for switching the measuring device into either the first or second switching status.

39. The switching activation device according to claim 36, wherein said activation portion is a two-tiered recessed portion that is complementary to at least one surface of the measuring device in shape and size such that the at least one measuring device undergoes switching to either a first switching status or to a second switching status when the activation portion of the switching activation device is proximate to the at least one surface of the measuring device.

* * * * *